United States Patent
Caro

Patent Number: 5,348,003
Date of Patent: Sep. 20, 1994

[54] METHOD AND APPARATUS FOR CHEMICAL ANALYSIS

[75] Inventor: Richard G. Caro, San Francisco, Calif.

[73] Assignee: Sirraya, Inc., San Francisco, Calif.

[21] Appl. No.: 940,188

[22] Filed: Sep. 3, 1992

[51] Int. Cl.$^5$ .............................................. A61B 5/00
[52] U.S. Cl. ..................... 128/633; 128/664; 128/665; 364/413.09; 364/550; 356/39
[58] Field of Search ............... 128/633, 634, 664, 665; 356/41, 39–40, 323–325; 364/413.09, 550

[56] References Cited

U.S. PATENT DOCUMENTS

| | | |
|---|---|---|
| 3,948,345 | 4/1976 | Rosencwaig . |
| 4,223,680 | 9/1980 | Jobsis . |
| 4,281,645 | 8/1981 | Jobsis . |
| 4,621,643 | 11/1986 | New, Jr. et al. . |
| 4,655,225 | 4/1987 | Dahne et al. . |
| 4,972,331 | 11/1990 | Chance . |
| 4,975,581 | 12/1990 | Robinson et al. . |
| 5,028,787 | 7/1991 | Rosenthal et al. . |
| 5,054,487 | 10/1991 | Clarke . |
| 5,077,476 | 12/1991 | Rosenthal . |
| 5,122,974 | 6/1992 | Chance . |

FOREIGN PATENT DOCUMENTS

0160768A1 11/1985 European Pat. Off. .

OTHER PUBLICATIONS

Jobsis et al., *Neurol. Res.*, 10:7–17 (1988), Near–infrared monitoring of cerebral oxygen sufficiency.
Mark, H., *Anal. Chem. Act.*, 223:75–93 (1989), Chemometries in Near–infrared Spectroscopy.
Haaland et al., *Anal. Chem.*, LX: 1202–1208 (1988), Partial Lease Squares Methods for Spectral Analysis. 2. Application to Simulated and Glass Spectral Data.
Haaland et al., *Analytical Chemistry*, LX:1193–1202 (1988), Title: Partial Least–Squares Methods for Spectral Analysis. 1. Relation to Other Quantitative Calibration Methods and the Extraction of Qualitative Information.

*Primary Examiner*—Angela D. Sykes
*Attorney, Agent, or Firm*—Flehr, Hohbach, Test, Albritton & Herbert

[57] ABSTRACT

A method and apparatus for determining the presence of an analyte in a medium or the composition of a medium wherein a volume of material is irradiated with temporally-modulated electromagnetic energy at multiple wavelengths. The electromagnetic radiation is detected after it has traversed a portion of the material. Representation signals related to the degree of absorption of electromagnetic energy at various wavelengths in the material and signals related to the path lengths travelled by the electromagnetic radiation in the material are generated, and signals representative of the optical absorption per unit path length at various wavelengths in the medium are derived. The derived wavelength dependence of the optical absorption per unit path length is compared with a calibration model, and the comparison is analyzed to derive concentrations of specific chemical species within the material and the presence of an analyte or composition of the medium. An output indicative of the concentration and composition is then provided.

44 Claims, 10 Drawing Sheets

METHOD AND APPARATUS FOR CHEMICAL ANALYSIS

FIELD OF THE INVENTION

This invention relates to methods and apparatus for chemical analysis, and more particularly, to a method and apparatus for the non-invasive quantitative determination of the presence or concentration of analytes (chemicals) in a multi-component sample material.

BACKGROUND OF THE INVENTION

Analysis of samples and determination of the concentration of components contained therein is a common and important process in chemistry and biology. Of particular importance is the analysis of biological fluids such as blood, urine or saliva to determine the concentrations of various components. Also of great importance is the measurement of the concentration of various chemical species embedded within a biological material such as tissue.

The chemical analysis of blood, urine, and other biological fluids is crucial to the diagnosis, management, treatment and cure of a wide variety of diseases and medical conditions including diabetes, kidney disease and heart disease. In the case of diabetes, monitoring of blood glucose levels several times per day is a necessary feature of management of the disease for many patients. In the case of people with diseases of the circulatory system, the analysis of various blood components is of importance both in diagnosis and in treatment. For example, the level of cholesterol compounds of various types in the blood of man has a strong correlation with the probability of onset of atherosclerosis. In patients with renal insufficiencies, urine analysis provides valuable information relating to kidney function. In a related application, the concentration of alcohol in blood is known to be correlated to an individual's physical response times and can provide information relating to, for example, the individuals fitness to drive a motorized vehicle.

At present, analysis of biological fluid for these and other applications is commonly invasively performed, that is by removing a sample of fluid, and subjecting it to one or more chemical tests. Typically, separate tests are required for each analyte to be measured. These tests require the use of consumable supplies and reagents and are moderately expensive. Often skilled technicians are needed to remove the fluid, and to perform the chemical tests. Frequently the tests are made in centralized clinical laboratories with resulting complexity of sample tracking, and quality control. In such circumstances there are additional problems relating to the potential change in the chemical composition of the fluid between its extraction and its analysis. Furthermore the turnaround time for such measurements can be undesirably long.

For many applications it would be desirable to be able to make real-time measurements of analytes in biological fluids or of the level of various clinically important chemicals in tissue. Ideally these measurements would be made non-invasively.

In addition to the above applications, there are a number of instances in which it is desirable to measure the local concentration of chemical species in tissue either in-vivo or in-vitro. In the case of victims of stroke or of head trauma it is desirable to be able to monitor the degree of brain edema as well as the concentration of various metabolic chemical species in the brain that act as indicators of brain function. These include various fatty acid compounds, water, blood, lactates, and various proteins and lipids. Other specific examples include the monitoring of metabolic function by measurement of tissue oxygenation, or the measurement of localized changes in tissue blood perfusion such as may be indicative of hyperplastic or neoplastic tissue.

Furthermore, it is widely believed that the ability to monitor certain changes in tissue chemical composition may lead to predictive tests for various types of cancer. Examples of such changes are the development of microcalcifications, specific changes in tissue chromophore types and concentrations, and specific variation in tissue hormone levels. Consequently non-invasive methods and apparatus which enabled measurements to be made of the chemical composition of tissue samples in-vivo would also be a very important development.

At present, when it is desired to monitor chemical levels in tissue such as in the brain, existing techniques require the use of Magnetic Resonance Imaging, CAT scan imaging or PET scan imaging. All of these techniques require the use of expensive equipment and do not allow bedside or continuous monitoring. Furthermore, for many conditions even these expensive and complex analytical techniques do not supply adequate information about the concentration of specific chemical species in the tissue.

An as yet unrealized goal for in-vivo monitoring of biological fluids and of the chemical composition of tissue would therefore be the development of methods and apparatus for the non-invasive, real-time measurement of analytes in a cost effective manner. For in-vitro fluid analysis the ability to make rapid measurements of single or multiple analytes could decrease analysis times, thus boosting the throughput of the clinical laboratories and reducing the cost of the analyses.

One approach to non-invasively determining the composition of tissue or of a biological fluid makes use of the interaction of electromagnetic radiation with the matter under examination. It is known that electromagnetic radiation having appropriate characteristics may interact with matter in two primary ways. As it passes through the material the radiation will be scattered and a portion of it will be absorbed. Different chemical species scatter and absorb to different degrees at different wavelengths. The physical composition of the medium will also effect its interaction with the radiation. A number of methods have been proposed that use optical radiation to probe tissue or fluid samples with the goal of determining the concentration of a component of the material by making use of known characteristics of the relationship between optical absorption of the medium and wavelength.

These prior methods generally share a number of common elements. A source of optical radiation emits light which enters the medium of interest and interacts with the medium, with the result that some radiation is absorbed by the medium. The incident light is chosen so that it contains wavelengths that are partially or wholly absorbed by the species for which the concentration is to be measured. Subsequently, the transmitted, reflected or scattered light is detected, and its intensity as a function of wavelength is measured. The measured intensity spectrum is then analyzed in order to yield information relating to the concentration of chemical species of interest within the medium.

Such prior art is represented, for example, by the development of the pulsed oximeter such as is described in U.S. Pat. No. 4,621,643 (New, Jr. et al., 1986). Such a device allows the determination of the percentage of oxygen saturation of the blood (i.e. the relative saturation).

In a series of patents, typified by U.S. Pat. No. 4,223,680 (Jobsis, 1980) and U.S. Pat. No. 4,281,645 (Jobsis, 1981), Jobsis has described the use of similar optical intensity measurements, to measure relative tissue oxygenation and metabolism by making use of the characteristic optical absorption spectra of both haemoglobin and of the cellular enzyme cytochrome (a,$a_3$). As with the work of New, the invention of Jobsis utilizes a small number of discrete wavelengths of light.

In extensions of this work, various techniques have been proposed in which many wavelengths of optical radiation would be used to measure the concentration of multiple analytes within a biological fluid or within biological tissue. After propagating into the medium and interacting with the component of interest the reflected or transmitted optical radiation is detected and the concentration of the component of interest is determined by comparison of the wavelength dependent intensity spectrum of the detected light with the known absorption spectra of a family of target components.

Such prior art is represented by U.S. Pat No. 4,975,581 (Robinson et al., 1990). An important aspect of such art is the use of sophisticated statistical techniques for the analysis of the measured optical absorption spectra. The study of these techniques is the science of chemometrics and the details of chemometric analysis are widely described in the scientific literature.

It is known to those skilled in the art of chemometrics that the number of independent chemical species that can be analyzed in a medium by the optical absorption spectroscopy techniques described above can not exceed the number of independent optical wavelengths used in the analysis. This is a fundamental limitation of the early inventions of New and of Jobsis. Since they rely on the use of a limited small number of discrete wavelengths, they can only be used in the case that optical absorption is primarily caused by a small number of chemical species.

This is the case for the measurement of oxygen in blood. However for most other chemical species of interest in biological media, this is not the case since there are numerous chemical species with similar and overlapping absorption spectra. In such instances the use of many wavelengths and multivariate analysis, such as is discussed in the work of Robinson et al, in U.S. Pat. No. 4,975,581, is essential.

All of the above prior art shares a fundamental flaw which makes its use for the analysis of chemical species in biological media suboptimal. The parameter measured by these techniques is the attenuation of light as it passes through a medium such as tissue or blood. From this attenuation is deduced the optical absorption of the medium. The optical absorption at a given wavelength is proportional to the absorption per molecule of chemical species times the concentration of the chemical times the distance travelled by the light in the medium. If we know the absorption properties of the chemical and we know the distance travelled by the light in the tissue, the individual chemical concentration can be deduced.

In biological media, and in fact in any scattering material, light is scattered multiple times as it traverses the medium. As a result, the path length travelled by the light is considerably longer than the direct geometric distance from light source to light detector. In fact, in typical tissue such as brain tissue, the light may travel 4 to 6 times that distance. Furthermore the distance travelled by the light will depend on the wavelength of the light and on the scattering and absorption properties of the medium at that wavelength. Consequently, in many cases optical spectroscopic techniques are able to provide only information about the optical absorption of a material and hence about the chemical concentration of a particular chemical species integrated over the path length travelled by the light in the medium. The reduction of that information to an absolute measurement of chemical concentration requires knowledge of the path length travelled in the medium.

This knowledge is not provided by any of the prior art techniques. Instead, they rely on the use of approximate estimates of path length, or measure parameters such as ratios of concentrations in which path length cancels. As a result, there are many important clinical situations in which it is desirable to obtain absolute concentrations of chemical species for which the prior art techniques are inadequate or insufficiently accurate. In this invention is described a method and apparatus for determining absolute chemical concentrations in highly scattering media by combining optical spectroscopic analysis with simultaneous path length analysis of the measured light.

OBJECTS OF THE INVENTION

It is, accordingly, the object of the present invention to provide a new and improved method and apparatus using electromagnetic radiation for the detection and quantification of various chemical species within biological media.

A specific object of the invention is to provide a new and improved method and apparatus for measuring the concentration in humans and animals of chemical species such as glucose, cholesterol, alcohol, bilirubin, ketones, fatty acids, lipoproteins, urea, albumin, creatinine, white blood cells, red blood cells, haemoglobin, blood oxygen, carboxyhemoglobin, inorganic molecules such as phosphorous or various drugs and pharmaceutical compounds in blood, urine, saliva or other body fluids.

A further object of the invention is to provide a new and improved method and apparatus for making such measurements non-invasively, quickly, easily and at reasonable cost.

A further object of the invention is to provide a new and improved method and apparatus for measuring the concentration in tissue of chemical species such as water, oxygenated haemoglobin, cytochrome a, $a_3$, glucose, cholesterol, alcohol, bilirubin, ketones, fatty acids, lipoproteins, urea, albumin, creatinine, white blood cells, red blood cells, inorganic molecules such as phosphorous or various drugs and pharmaceutical compounds, insulin, various proteins and chromophores, microcalcifications, and various hormones.

A further object of the invention is to provide a new and improved method and apparatus for making such measurements non-invasively, quickly, easily and at reasonable cost.

A further object of the invention is to provide a new and improved method and apparatus for measuring the concentration of a variety of chemical components in a complex mixture of fluid media simultaneously, or consecutively within a short time duration.

SUMMARY OF THE INVENTION

A method for determining the chemical composition of a material are disclosed. The method generally comprising the steps of irradiating a volume of the material with temporally-modulated electromagnetic energy at multiple wavelengths; detecting the electromagnetic radiation after it has traversed a portion of the material; generating representation signals related to the degree of absorption of electromagnetic energy at various wavelengths in the medium; generating representation signals related to the path lengths travelled by the electromagnetic radiation in the material; deriving from said representational signals further signals representational of the optical absorption per unit path length at various wavelengths in the medium; comparing the derived wavelength dependence of the optical absorption per unit path length with a calibration model built up either from a priori principles or by means of measurements made on a set of calibration samples; analyzing said comparison to derive concentrations of specific chemical species within the material; and providing an output indicative of said concentrations.

An apparatus for determining the presence of an analyte in a medium or the composition of a medium is disclosed. The apparatus generally comprises means for irradiating a volume of the material with temporally-modulated electromagnetic energy at multiple wavelengths; means for detecting the electromagnetic radiation after it has traversed a portion of the material; means for generating representation signals related to the degree of absorption of electromagnetic energy at various wavelengths in the material; means for generating representation signals related to the path lengths travelled by the electromagnetic radiation in the material; means for deriving from said representational signals further signals representational of the optical absorption per unit path length at various wavelengths in the medium; means for comparing the derived wavelength dependence of the optical absorption per unit path length with a calibration model built up either from a priori principles or by means of measurements made on a set of calibration samples; means for analyzing said comparison to derive concentrations of specific chemical species within the material and to determine the presence of an analyte or the composition of the medium; and means for providing an output indicative of said concentrations and composition.

BRIEF DESCRIPTION OF THE DRAWINGS

The foregoing and other objects of the invention will be understood from the following description when read in conjunction with the accompanying drawings in which.

DETAILED DESCRIPTION OF THE PREFERRED EMBODIMENT

This invention involves the use of electromagnetic radiation, for example optical radiation, to determine the concentration or presence of one, several, or many chemical species within a complex material. The material may be a solid or a liquid or a gas, or a mixture of solid, liquid and gas phase materials. Unlike all prior art techniques, this invention can be used to analyze highly scattering materials such as biological media. To do this the invention relies on the measurement of optical absorption and of optical path length distribution in the material at multiple wavelengths. From these measurements are derived the optical absorption per unit path length of the material at multiple wavelengths. This data is compared with a calibration model using the techniques of chemometric analysis such as Partial Least Squares analysis, Principal Component Regression analysis or related techniques. By means of such analysis, the concentrations of various chemical species within the material can be derived from the measured data. The invention then provides an output indicative of these concentrations.

The invention is useful for analyzing the composition of a material generally but finds particular utility with respect to biological systems or materials because the apparatus and method are non-invasive and do not subject the material to any apparent damage during the analysis. When the term medium or material is used, such use includes biological tissues or fluids either in-vivo or in-vitro, as well as other materials. Furthermore, the use of the term "tissue" refers in an exemplary fashion to a biological material; however, it should be understood that unless otherwise stated, the method or apparatus so described is not limited to biological tissues.

Figure 1:
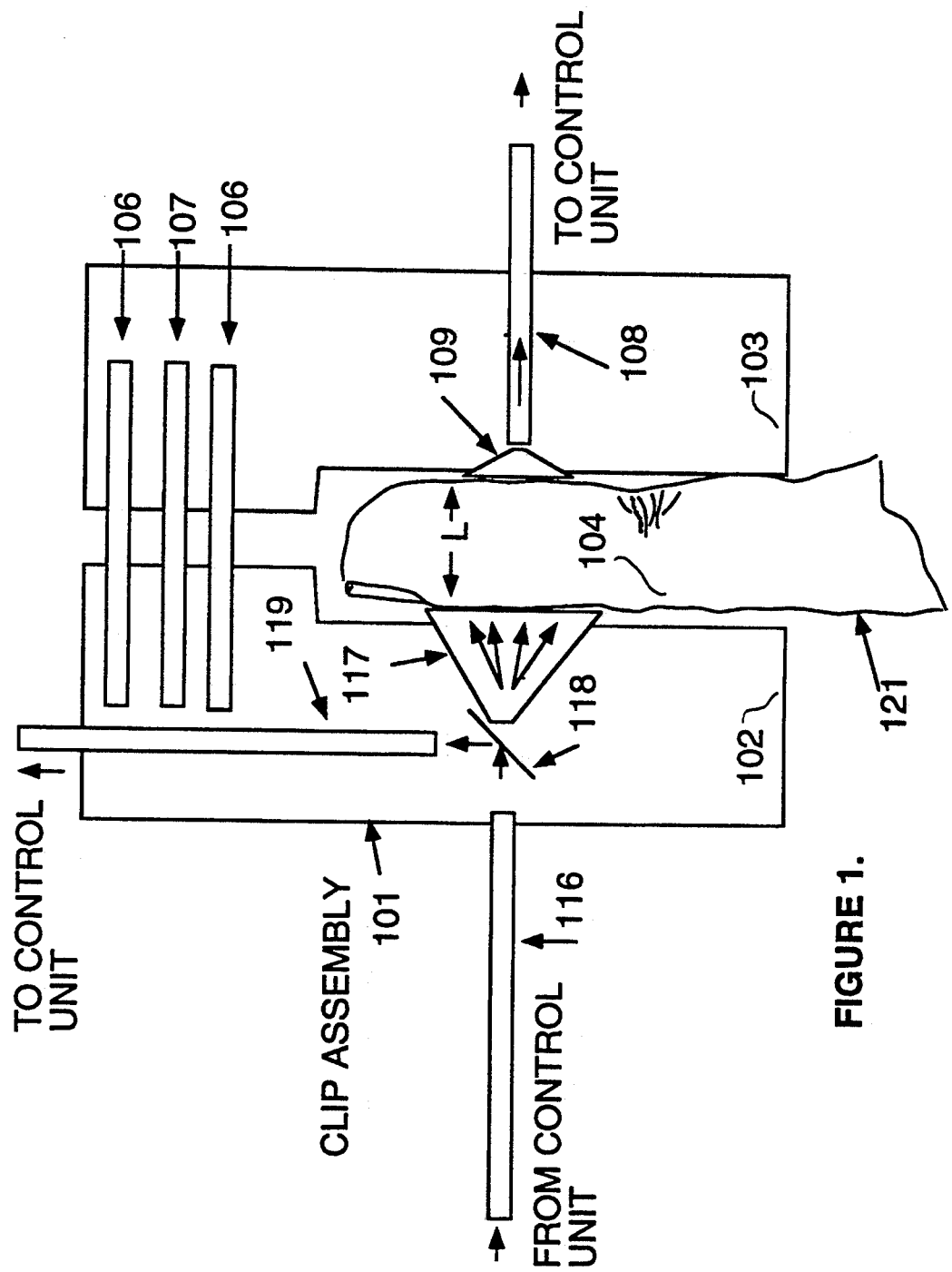
FIG. 1 is an illustration which shows a portion of the apparatus, particularly the clip assembly, associated with a first embodiment of the invention.

With respect to FIG. 1 there is illustrated a first embodiment of an apparatus for practicing the present invention. A clip assembly 101, having opposing left clip assembly 102, and right clip assembly 103, is removably attached to a sample of tissue, for example, a finger 104, by use of spring loading 106 which causes the opposing left and right clip assembly sections 102, 103 to contact the tissue 104. The form of the clip may be altered to suit the particular attachment site, and may contain more sections or jaws and sections or jaws of different shape or size as necessary. The spring loading 106 may be accomplished by any conventional spring or resilient material, such as for example, metal flat or coil springs, deformed plastics, resilient foams, rubber disks or bands, and so on. Hinges and/or pivots may also be used advantageously to achieve the desired application or attachment pressure, and in such cases the placement of the spring loading 106 will be such as to take advantage of the leverage. It may also be desirable to achieve contact without spring loading 106, by the use of an adhesive means interposed between the sections of the clip assembly 101 and the tissue 104.

When the apparatus and method of the invention are applied to a determination of the composition of blood, and there is a choice in site selection, the site is optimally chosen so that the appendage is relatively thin and is well vascularized so that there is a considerable volume of blood contained within the tissue. For example, the tissue 104 may be a body appendage such as the ear lobe, nose, finger, or a fold of skin. A potentiometer 107, or other means for sensing the separation of the left and right clip assembly sections 102, 103 of the clip assembly 101, is provided to monitor the tissue thickness, L, and may be contained within the clip assembly 101.

Figure 2:
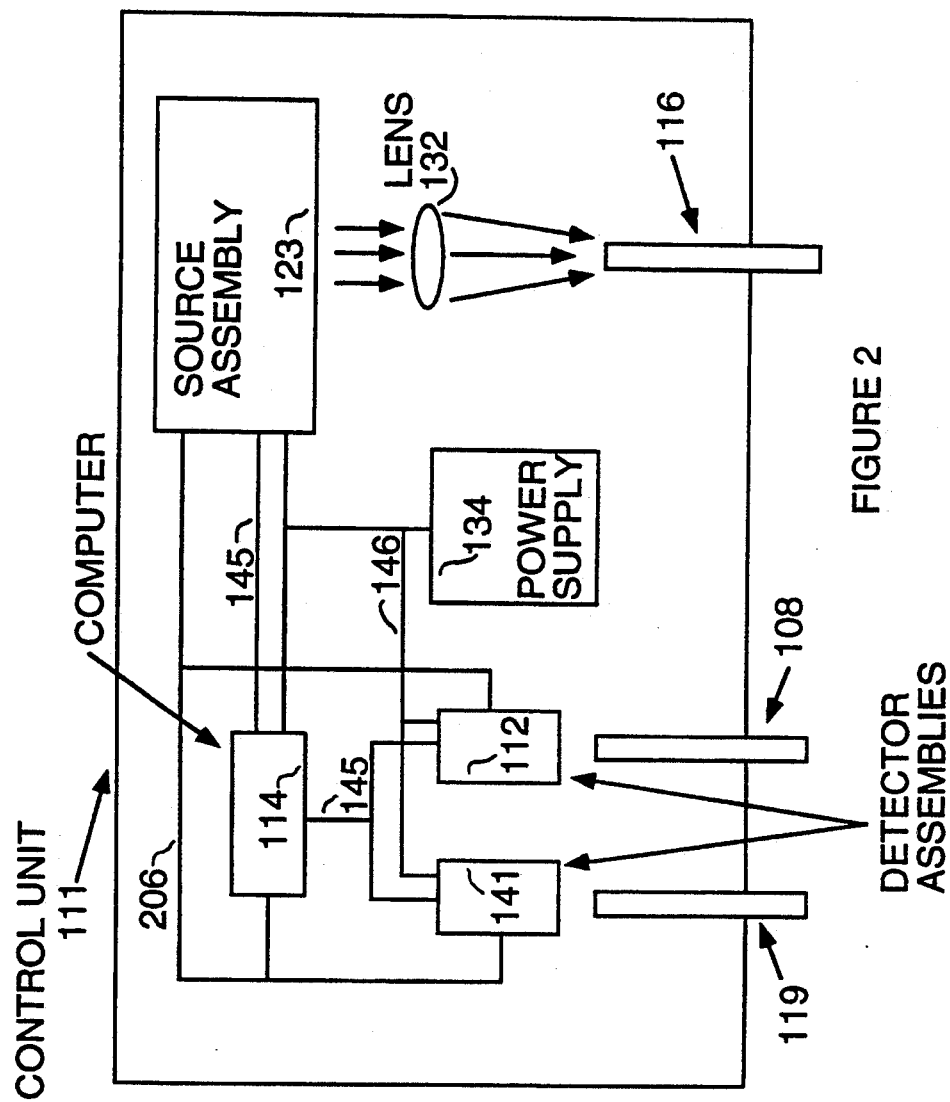
FIG. 2 is an illustration which shows a portion of the apparatus, particularly the control unit, associated with a first embodiment of the invention.

Attached to the clip assembly 101 is fiber optic means 116 which delivers electromagnetic radiation in the form of light from the control unit 111, FIG. 2, to the tissue 104. Under some circumstances the beam from fiber optic means 116 may be altered, such as by expanding or compressing or focusing the beam by beam expansion, compression or focusing means 117, such as a lens system, tapered fibers, or other conventional optical beam shaping devices, so as to illuminate the tissue sample over an area different than would be achievable from the unaltered output of fiber optic means 116.

A portion of the light emanating from optical fiber means 116 is split off by a beamsplitter 118 and collected by a second optical fiber means 119. Means for collecting and directing the light from beamsplitter 118 such as a lens may optionally be used to direct the light into the entrance face of optical fiber means 119. The second optical fiber means 119 is also connected to the control unit 111, FIG. 2. The light intensity measured at the control unit 111 from optical fiber 119, is linearly related by a constant multiplicative value to the light intensity incident on the tissue surface 121. The multiplicative constant is known generally from the design of the apparatus, and may be determined more precisely from a calibration procedure. Thus, the light intensity is continuously monitored.

Also attached to the clip assembly is fiber optic means 108, positioned so as to collect light emanating from the tissue sample 104, and positioned roughly opposite to fiber optic means 116. Light incident on the sample 104 from fiber optic means 116 passes through a portion of the sample 104, exits the sample and is collected by optical collection means 109 in the form of a lens system, tapered fiber, or other beam collection means, and is directed into fiber optic means 108. The collected light is transmitted through fiber optic means 108 to the control unit 111 in FIG. 2.

With respect to FIG. 2 there is illustrated a control unit 111, which comprises several components. It may be desirable to include substantially all the components into a single unit, possibly even incorporating some or all the electronics into the body of clip assembly 101. The control unit 111 contains a source assembly 123 of temporally modulated radiation to be described with respect to FIG. 3. In this embodiment the radiation is in the optical wavelength range, such as between 250 nm and 3000 nm. Light is emitted from source assembly 123, passes through lens 132 and is focused into optical fiber means 116. This light is then incident on the tissue 104 enclosed by the clip assembly 101 of FIG. 1. The light collected by optical fiber means 119, FIG. 1, is transmitted to the control unit 111 where it is detected by a detector assembly 141. The light incident on the tissue from fiber optic means 116 passes through a portion of the tissue 104. After emanating from the tissue 104, a portion of that light is collected by optical fiber means 108, FIG. 1, and is transmitted to the control unit 111 where it is detected by a detector assembly 112.

In detector assembly 141, the incident optical signal is detected, measured and analyzed. The output from the detector assembly 141 is a series of electrical signals in a digital form, which are transmitted to the computer 114 either serially or in parallel for processing, analysis and data storage. In detector assembly 112, the incident optical signal is detected, measured and analyzed. The output from the detector assembly 112 is a series of electrical signals in a digital form, which are transmitted to the computer 114 either serially or in parallel for processing, analysis and data storage.

Control signals are provided between each of the assemblies 123, 112, 141 and the computer 114 in FIG. 2 to provide synchronization and proper data transfer among the several components of the apparatus. There are control lines 145 provided between computer 114 and each of the assemblies 123, 112, and 141. Power to drive all of the subsystems illustrated in FIG. 2 is provided by a built in power supply 134 connected to each subsystem by power lines 146. Multiple power supplies may also be employed to power the different components. Additional Control lines, 206, connect the light source assembly, 123, with the assemblies 114, 141, and 112.

Figure 3:
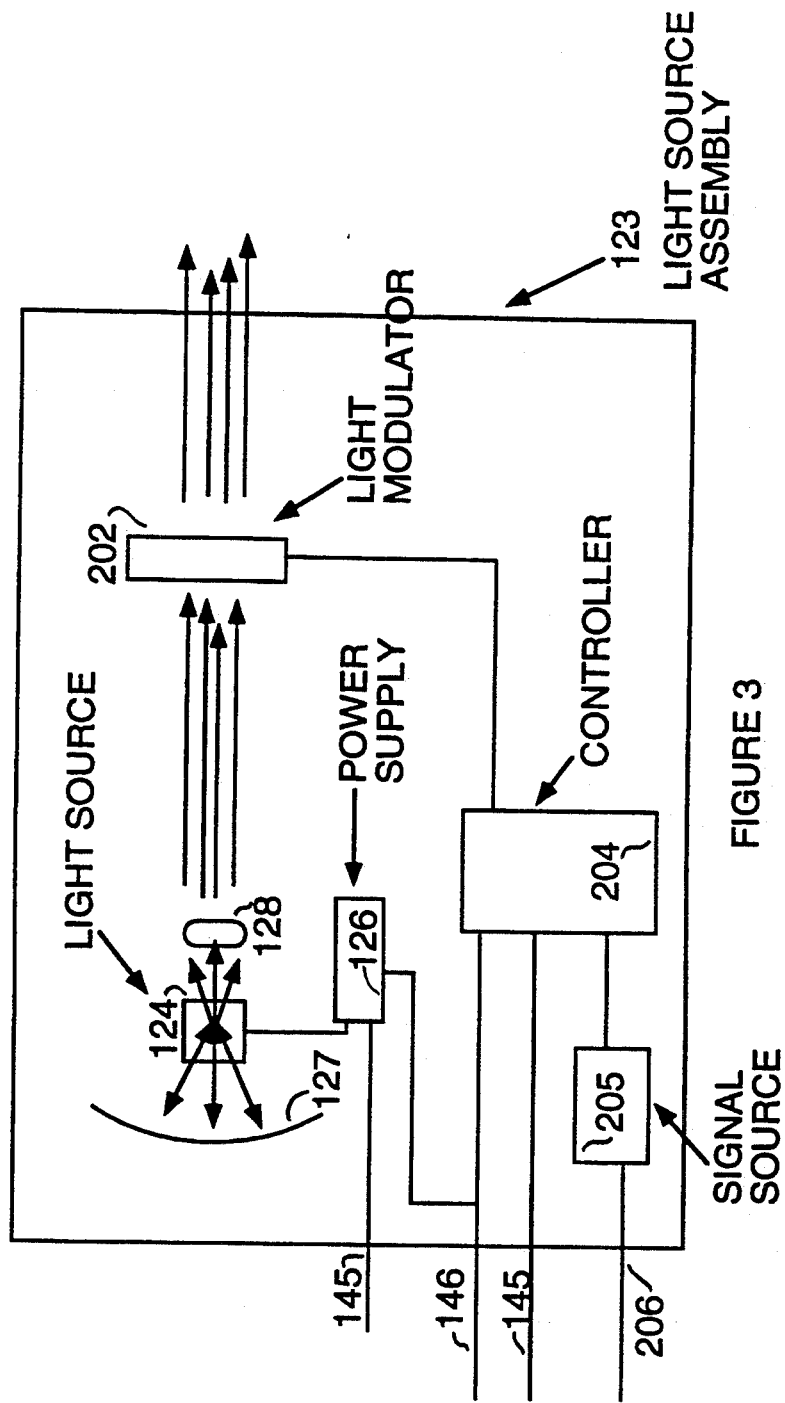
FIG. 3 is an illustration which shows a portion of the apparatus, particularly the light source assembly, associated with a first embodiment of the invention.

With respect to FIG. 3, there is illustrated the light source assembly 123 referred to in FIG. 2. This light source assembly contains a light source 124 which emits light containing wavelengths within the range of 250 nm and 3000 nm. Light from this source passes through a light modulator 202 before exiting the assembly 123 in the form of a collimated beam of temporally modulated light containing a range of wavelengths within the range of 250 nm to 3000 nm.

In this embodiment source assembly 123 includes an intense light source 124 such as an Argon arc lamp, or a xenon arc-lamp, for example Hamamatsu model L2274 or L2189 or a tungsten lamp, for example Hamamatsu model L2192. In this embodiment light source 124 is effectively on continuously during operation. In other embodiments, light source 124 may be pulsed. Light source 124 is driven by means of a source power supply 126.

In this embodiment the light from light source 124 is refocused by concave reflector 127 then collimated by a source lens 128. The geometry of the light source 124, concave reflector 127, and source lens 128, direct the radiation so that it is incident on a light modulator 202. Concave reflector 127 may have a spectrally selective reflective coating such that any undesirable spectral components, such as thermal infra-red spectral components, are not reflected into the source lens 128. Other spectral filters such as heat absorbing glass (not shown) may be similarly interposed in the optical system.

In this embodiment light modulator 202 is an electro-optic modulator, consisting of a wide aperture double-crystal Pockels cell and associated polarizers, such as is sold by ISS of Champaign Illinois. The detailed choice of modulator 202 is dependent on the light wavelength range desired and upon the range of modulation frequencies required. In other embodiments acousto-optic modulators or other means for modulating light rapidly could be used. The modulator is driven by modulator controller 204. The modulator controller is driven by an electronic control signal deriving from a source 205, producing a repetitive electronic drive signal of a particularly stable nature. In this embodiment the source 205 is a stable radio frequency generator such as Stanford Research Systems model DS345 function generator. A reference signal from source 205 is transmitted to the computer 114 and to the detector assemblies 141 and 112 by means of electrical cables 206.

The output of assembly 123 is a collimated beam of light that can be focused into fiber optic means 116 by a lens 132. This light beam contains multiple wavelengths and can be modulated by means of the modulator 202. In this embodiment, the light beam contains essentially a continuum of wavelengths between 300 nm and 3000 nm as emitted from the xenon arc-lamp light source. The temporal modulation pattern can be varied depending on the type and geometry of the tissue sample 104. A typical modulation pattern would be a sinusoidal modulation pattern with a frequency of 40 MHz. Other modulation frequencies from 1 MHz to 500 MHz would also be appropriate in some instances.

Other modulation patterns could consist of a train of pulses of short duration with essentially zero light transmitted through the modulator between pulses, or of a repetitively modulated signal of a non-sinusoidal nature. In the former case, pulsewidths as short as one picosecond could be advantageously used, with shorter pulses also being appropriate where possible. Longer pulses can also be used depending on the geometry of the tissue sample 104. For most geometries pulses should be shorter than one microsecond. The interpulse separation can be long and is not critical except in so much as it effects the rate of data collection. In the case of non-sinusoidal periodic modulation, modulation waveforms such as square waves or a variety of other periodic waveforms can be used.

Figure 4:
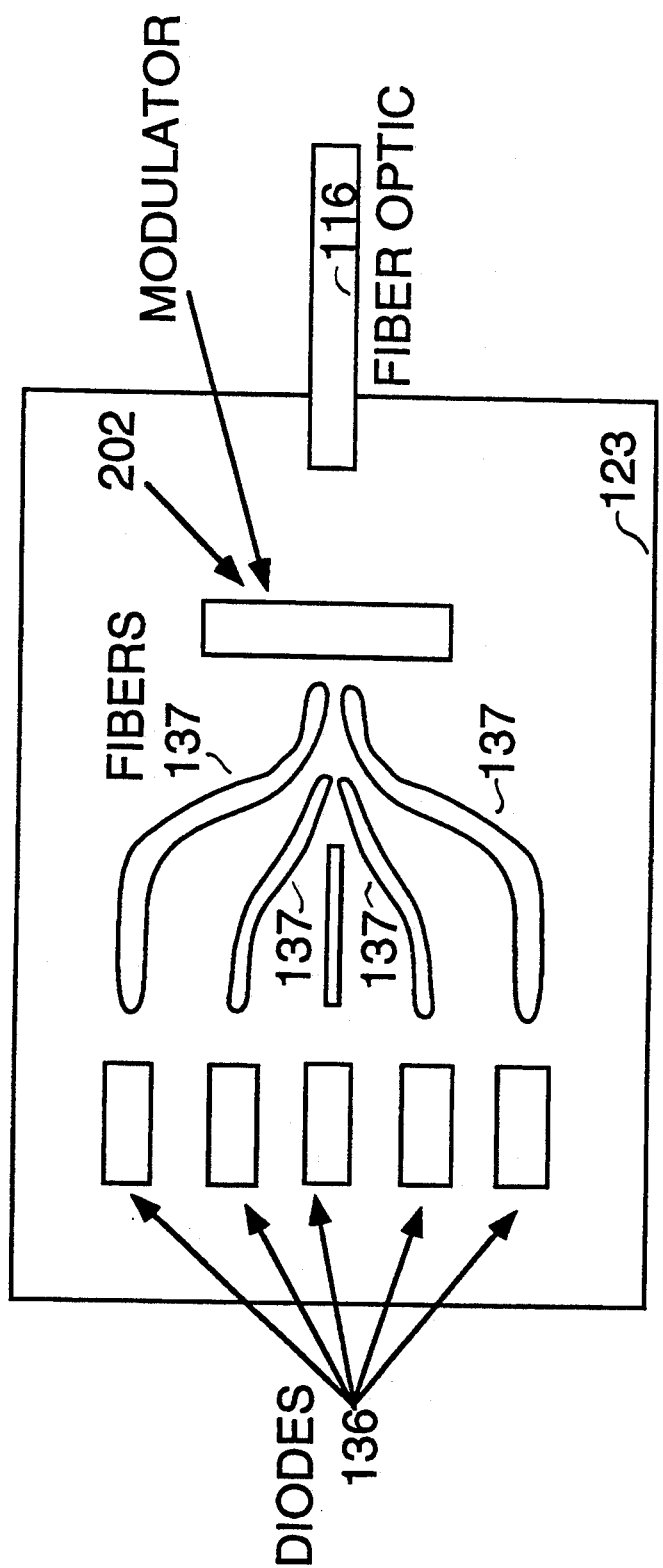
FIG. 4 is an illustration which shows an embodiment of the apparatus according to this invention which employs light emitting diodes.

There are several possible embodiments for the radiation source assembly 123. In an alternative embodiment the light source 124 is replaced by one or many diode lasers or light emitting diodes (LED's) 136 as illustrated in FIG. 4. In such an alternative embodiment light from the diode lasers or LED's 136 is transmitted through the optical modulator 202. Multiple fiber means 137 are alternatively used to couple the multiple sources to the optical modulator 202.

In yet another embodiment solid state lasers or crystal lasers are used as the light source. For example Titanium: Sapphire or Alexandrite or Forsterire or Cobalt Magnesium Fluoride or chromium doped lithium-strontium aluminum fluoride or chromium doped lithium-calcium aluminum fluoride lasers are all tunable in the spectral region of interest.

In yet another embodiment such a laser crystal is operated below threshold as a super luminescent bright source of broadband radiation.

In yet another embodiment, broad band light over a wide wavelength range is generated using nonlinear optical processes. For example, a short, intense pulse of laser light such as from a Q-switched laser is passed through a nonlinear medium such as a fiber-optic where Raman shifting occurs and a continuum of light is generated as a result. Alternatively an optical parametric oscillator can be used to generate varying wavelengths of light at longer wavelengths than initially generated by a tuneable laser.

In yet another family of embodiments, the light source itself is modulated rather than passing the light through a separate modulator. An example of this would be the use of diode lasers or LED's as shown in FIG. 4, in which the drive current to the individual diodes is modulated resulting in a modulated optical output. Alternatively, a light source could be used that consists of a pulsed arc lamp or other type of electrical discharge lamp, in which the lamp can be repetitively modulated, or pulsed, by modulating the drive current to the lamp.

Each of these alternative embodiments for the light source assembly 123 provides a system capable of producing temporally modulated beams of light that can be coupled into fiber optic means 116. In each case the light beam transmitted through the fiber optic means 116 contains multiple wavelengths of light. In each case, a reference signal is transmitted from the light source assembly 123 to the computer 114 and to the detector assemblies 141 and 112 by means of cable 206. This reference signal contains information concerning the modulation frequency, phase and waveform of the light.

The light from light source assembly 123 is transmitted to the tissue sample 104. A portion of this light is returned to the control unit 111 by means of the fiber optic means 119. This light is detected and analyzed in detector assembly 141 and is representative of the light incident on the tissue. A further portion of light is transmitted through a portion of the tissue sample 104 and returned to the control unit 111 by means of fiber optic means 108. This light is detected and analyzed by detector assembly 112 and is representative of light that has propagated through the tissue sample. A comparison of the information detected in assemblies 141 and 112 thus yields information about the optical absorption properties of the sample 104.

Figure 5:
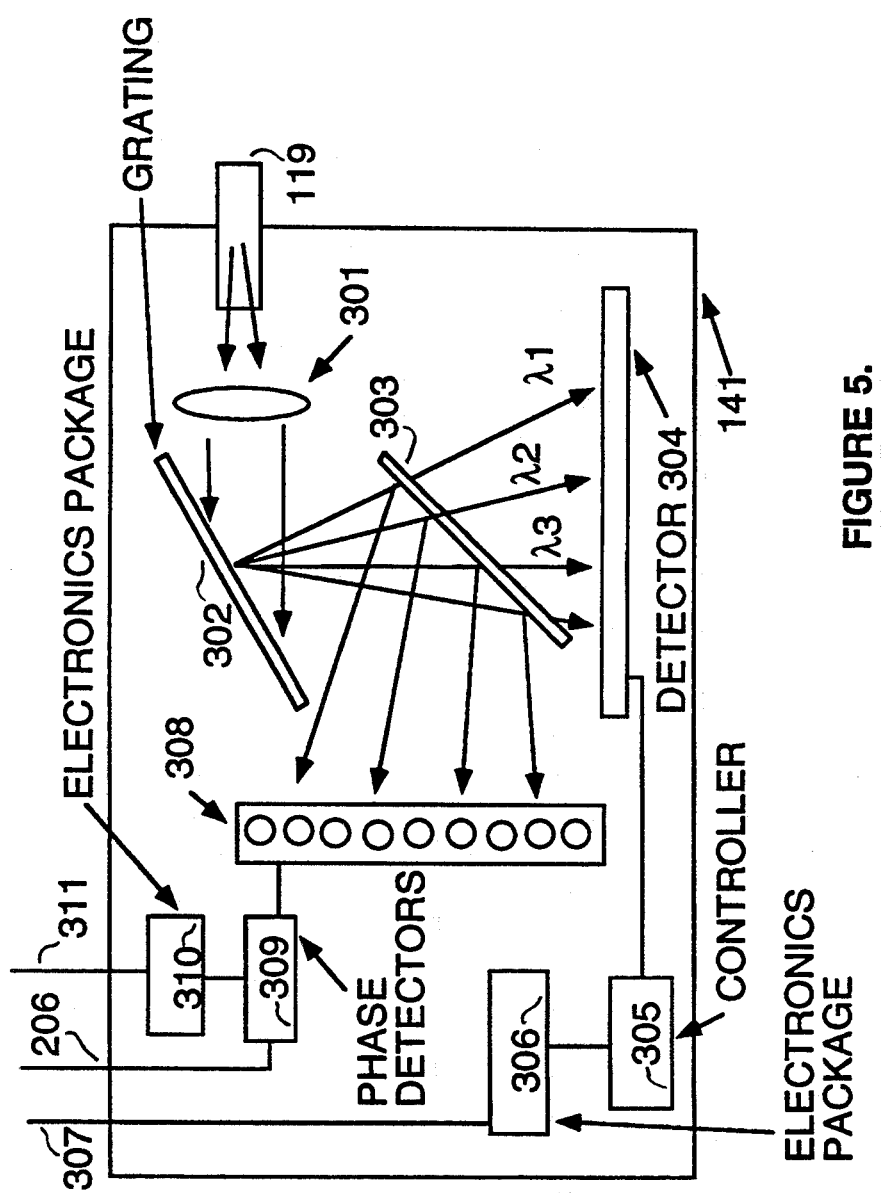
FIG. 5 is an illustration which shows a portion of the apparatus, particularly the detector assembly, associated with a first embodiment of the invention.

Detector assembly 141 is illustrated in FIG. 5. The light entering the detector assembly 141 from fiber optic means 119 passes through a lens 301, from which it emerges as a collimated beam of light. This light is incident on a wavelength dispersive means 302, represented in this embodiment by a diffraction grating. In other embodiments this element could be a prism, optoacoustic tuning element, set of optical filters, or other means for spatially dispersing the component wavelengths of the incident light. After dispersion by this optical element the light fans out with different wavelengths travelling along paths at different angles from the initial incident angle of the beam. The dispersed light is separated into two beams by a beamsplitter 303 in the form of a Fresnel reflector or other broadband partial reflector.

One of the two resultant beams is incident on a detector array 304. In this embodiment this array is in the form of a silicon diode array such as made by EG&G. In other embodiments, the array may be replaced by a CCD camera, or by a pyroelectric array or by an array detector with detector elements of lead selenide, lead sulphide, Indium antimonide or other photosensitive material. The choice of detector type is dependent on required wavelength sensitivity and available light intensities for a given application. In some embodiments where especially broad spectral coverage is required, multiple detector arrays of differing materials may be used, each sampling a portion of the wavelength dispersed beam.

The output from the detector array passes through the detector controller, 305. The controller converts the detected light signals to an array of electrical signals representing the light intensity incident on the array as a function of position across the array. By using calibration procedures to determine the relationship between dispersed wavelength and spatial position, the controller 305 can generate an array of output values corresponding to light intensity as a function of wavelength. In operation, the controller 305 reads information from the detector array 304 in either a sequential or parallel fashion, such information consisting of an array of analog electrical signals representing the intensities of light detected at the elements of the detector array 304. This array of analog signals is digitized in electronics package 306. The digital signals may be amplified, filtered or otherwise processed in package 306 prior to digitization in order that they be made compatible with the analog-to-digital converters contained therein. The array of digital signals thus produced corresponds to an array of light intensity values $I_1(\lambda)$ at various wavelengths, $\lambda$. These signals are transmitted to computer 114 sequentially by means of cable 307. In other embodiments, the signals may be transmitted to computer 114 simultaneously by means of a parallel interface.

The second beam reflected from element 303 is incident on an array of detectors 308 capable of generating time varying signals at the modulation frequency of the light. Each of the detector elements of array 308 generates a time varying signal which is fed into one of an array 309 of electronic processing units capable of measuring the phase delay between the detected optical signal and a reference signal derived from the light source assembly 123 and transmitted to array 309 by means of cable 206. After calibration of the system, the resultant output of this detection system is an array of values representing the average phase shift $\phi_1(\lambda)$ of detected light as a function of wavelength, $\lambda$. These values are digitized and electronically processed in the electronics package 310 prior to transmission to the computer 114 by means of cable 311.

It is not always necessary for the number of detector elements in array 308 to equal the number of detector elements in array 304. Under some conditions, it may be adequate to measure a phase shift at several wavelengths spanning the range of wavelengths of interest and then interpolate between those wavelengths. Under other conditions, it may be adequate to measure a phase shift at a single wavelength and from that measured phase shift, deduce phase shifts at other wavelengths using certain approximate relationships derived during calibration.

In other embodiments, it may be possible to combine arrays 304 and 308 into a single array, or it may be adequate to measure the average phase delay of the light without taking wavelength dependence into account. In such a case, beamsplitter 303 could be positioned prior to optical disperser 302, and detector array 308 and processor array 309 could be replaced by single element electronics.

Detector assembly 112 is essentially identical to detector assembly 141. The light transmitted from clip assembly 101 by fiber optic means 108 is analyzed in detector assembly 112. The resultant output from assembly 112 is an array of measurements of intensity $I_2(\lambda)$ and phase delay $\phi_2(\lambda)$ as a function of wavelength, $\lambda$.

Figure 6:
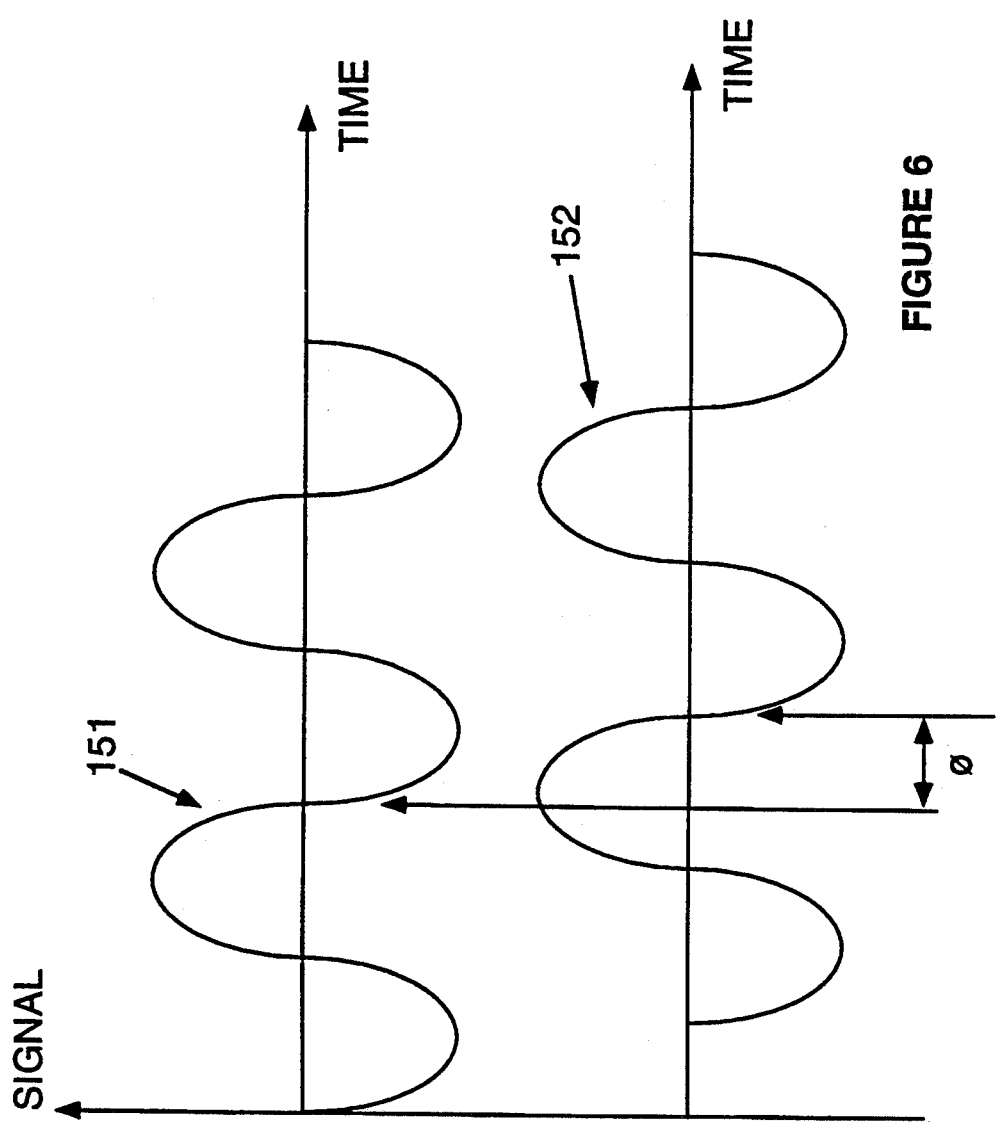
FIG. 6 is an illustration which shows an example of a typical detected modulated optical signal.

In FIG. 6 is illustrated a typical modulated signal 152 as detected by an element of detector 308 in assembly 112 together with a typical modulated signal 151 as detected by an element of detector 308 in assembly 141 under the conditions where the light source assembly 123 generates a sinusoidally modulated light beam. The phase shift $\phi(\lambda)$ between the two signals is shown in FIG. 6. The phase shift, $\phi(\lambda)$, is correlated to the average delay experienced by light as it passes through the tissue 104 and includes the effects of scattering on the total path travelled by the light. This phase shift is equal to the difference between the phase shift $\phi_2(\lambda)$ measured in detector assembly 112 and the phase shift $\phi_1(\lambda)$ measured in detector assembly 141.

Figure 7:
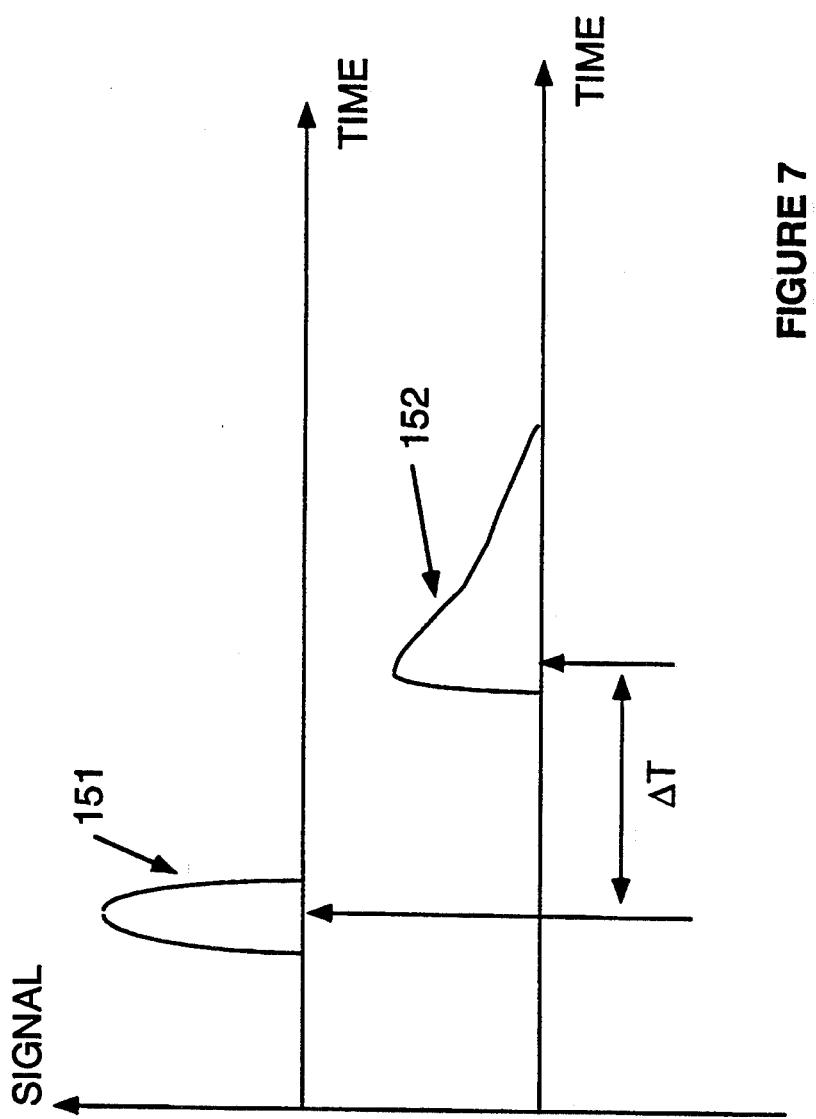
FIG. 7 is an illustration which shows an example of a typical detected pulsed optical signal.

In FIG. 7 is illustrated the analogous signals under circumstances where the light source assembly 123 generates a series of discrete short pulses of light. In this case the light detected by detector assembly 112, represented by signal 152 in FIG. 7, has a temporal shape that is lengthened with a peak which is delayed with respect to the signal 151 detected by detector assembly 141 by a time interval $\Delta t$.

In operation the clip assembly 101 is attached to a sample of tissue 104, a patient's earlobe for example, and firmly held to the earlobe tissue 104 as a result of the spring loading 106. In other embodiments, the clip assembly could be attached to larger portions of the anatomy, for example to the head of an infant or even an adult. During operation, the light source 124 is switched on, and the detector assemblies 141 and 112 begin to collect data. After sufficient time has elapsed for adequate data collection, the analysis of the detected signals by the computer 114 begins. At this point the light source may be switched off.

The data fed into the computer from detector assemblies 141 and 112 represents a number, n, of measurement data sets, each of which is associated with a specific wavelength. At a given wavelength, $\lambda$, the information contained in the data sets includes intensity of light incident on the tissue, $I_1(\lambda)$, and intensity of light exiting the tissue, $I_2(\lambda)$, as well as the phase difference $\phi(\lambda)$ between the light incident on the tissue and the light exiting the tissue. Now from Beer's law, the optical absorption coefficient of the sample at a given wavelength, $\lambda$, is given by $a(\lambda)$, where $$a(\lambda) = [1/L(\lambda)] * [ln[I_1(\lambda)/I_2(\lambda)] + A(\lambda)] \quad (1)$$

where $L(\lambda)$ is the optical path length of light of wavelength, $\lambda$, in the medium, and $A(\lambda)$ is a wavelength dependent parameter dependent on the degree of scattering in the medium as well as on the degree of reflection and the tissue geometry of sample 104.

When light travels through the tissue sample 104, it is scattered multiple times. As a result, the optical path through the medium greatly exceeds the geometric path length through the sample. In an example such as the head of an infant, the optical path length is known to exceed the geometric path length by a factor of at least five. In the two detector assemblies 141 and 112, the phase shifts are measured of light incident on, and exiting the tissue sample 104. The difference between these phase shifts $\phi_1(\lambda)$ and $\phi_2(\lambda)$ is directly related to the optical path length between the entrance faces of fiber optic means 119 and 108. Using calibration techniques to compensate for offsets and making use of the measurement of geometric path length made by potentiometer 107 in FIG. 1, it is possible to derive the component of phase shift, $\phi(\lambda)$, that is attributable to optical propagation through tissue. Now, for a given modulation frequency, f, of light incident on the tissue 104, it is well known to those skilled in the art of Frequency-domain Fluorimetry that when c is the speed of light in tissue 104, that $$\phi(\lambda) = 2\pi f L(\lambda)/c \qquad (2)$$

Equation 2 holds so long as the frequency of excitation is such that $2\pi f < < \mu c$ where $\mu$ is the absorption coefficient in the medium. For typical values of $\mu$ in the range of (0.1–100) cm$^{-1}$, this requires modulation frequencies less than (0.3–300) GHz.

To use an illustrative example, for a modulation frequency of 50 MHz, and with the head of a neonatal infant as the test sample, 104, observed optical path lengths through the head of the infant are approximately 10 cm for a wavelength of light of 816 nm. This corresponds to a phase shift of $\phi=0.16$ radian, or 1/40 of a cycle and is readily achievable with conventional phase-sensitive detection techniques.

In an alternate embodiment where the light source assembly 123 generates a series of pulses of light with detected signals as illustrated in FIG. 7, the optical path length through the sample 104 can be derived from the formula $$L(\lambda) = c \, \Delta t(\lambda) \qquad (3)$$

While the measurement of L in the embodiments described here involves the measurement of a phase shift or of a time delay as shown in FIGS. 6 and 7, alternative measurements may be made that are related to path length in a different manner. For example, the time delay between the onset or the termination of the pulses shown in FIG. 7 could be measured, or a more complex function of phase shift could be determined which included measurement of phase shift as a function of varying modulation frequency.

The measurements obtained during operation of this invention thus provide all of the information required to solve equation (1) with the exception of $A(\lambda)$. Since this is typically a slowly varying function of $\lambda$, analysis of the derivatives of the terms of equation (1) allows the determination of $a(\lambda)$. For example, over small ranges of )$\lambda$, equation (1) reduces to equation (4), soluble for $a(\lambda)$.

$$d/d\lambda\{[a(\lambda)*L(\lambda)]\} = d/d\lambda\{\ln[I_1(\lambda)/I_2(\lambda)]\} \qquad (4)$$

In operation, then, this embodiment enables the determination to be made of the absorption coefficient of the sample 104 as a function of wavelength $\lambda$.

Once the absorption coefficient of the medium has been determined as a function of wavelength over the wavelength range of interest, it is necessary to correlate the absorption spectrum of the medium with a model data set including known absorption spectra of the various components of interest as well as absorption spectra of a variety of complex samples of partially known composition representative of the range of potential compositions of the sample to be measured. As a result of this correlation, the absolute and relative concentrations of a variety of chemical species within the medium can be accurately determined.

In making this correlation, the computer, 114, employs a variety of algorithms depending on the tissue and component species that are of interest. The correlation techniques and algorithms are typical of those employed in the field of chemometrics and include a variety of univariate and multivariate analysis techniques such as the use of discriminant algorithms, multiple regression algorithms, the use of principal component regression analysis and the use of partial least squares analysis. Such techniques are referenced in Robinson et al. (U.S. Pat. No. 4,975,581) and discussed by Mark (Anal. Chem. Act. 223,75–93, 1989) as well as by Haaland et al. in Analytical Chemistry, Vol. LX, p.1193 (1988) and in Analytical Chemistry, Vol. LX, p.1203 (1988).

Typically these correlation techniques employ absorption data obtained at several separate wavelengths. This multivariate approach has the important advantages of increasing accuracy and precision while at the same time allowing the use of techniques for the detection, recognition and exclusion of "outlier" samples. Such "outlier" samples are those samples that do not exhibit typical correlations between absorption properties and component concentrations. Their identification is important in the development of an accurate calibration model. It is also important to identify situations where the sample to be analyzed (the patient, for example), is itself an outlier and to provide notification in the rare cases where such samples can not be correctly analyzed as a result.

The model data set used by the computer 114 to deduce component concentrations from measured absorption coefficients can be developed during manufacture of the invention and stored in the memory of the computer at that time. Alternatively, the model data set can be made to be specific to a particular individual, or class of individuals. In that case the invention may include the provision for calibration of its model data set from time to time during use. The invention may include provision for input of user specific model data sets. This input could be in the form of an external memory device that can be attached to the invention, electronic communication with a device that contains said patient specific model data set, or a plug-in module consisting of electronic memory in which said data set is contained.

Figure 8:
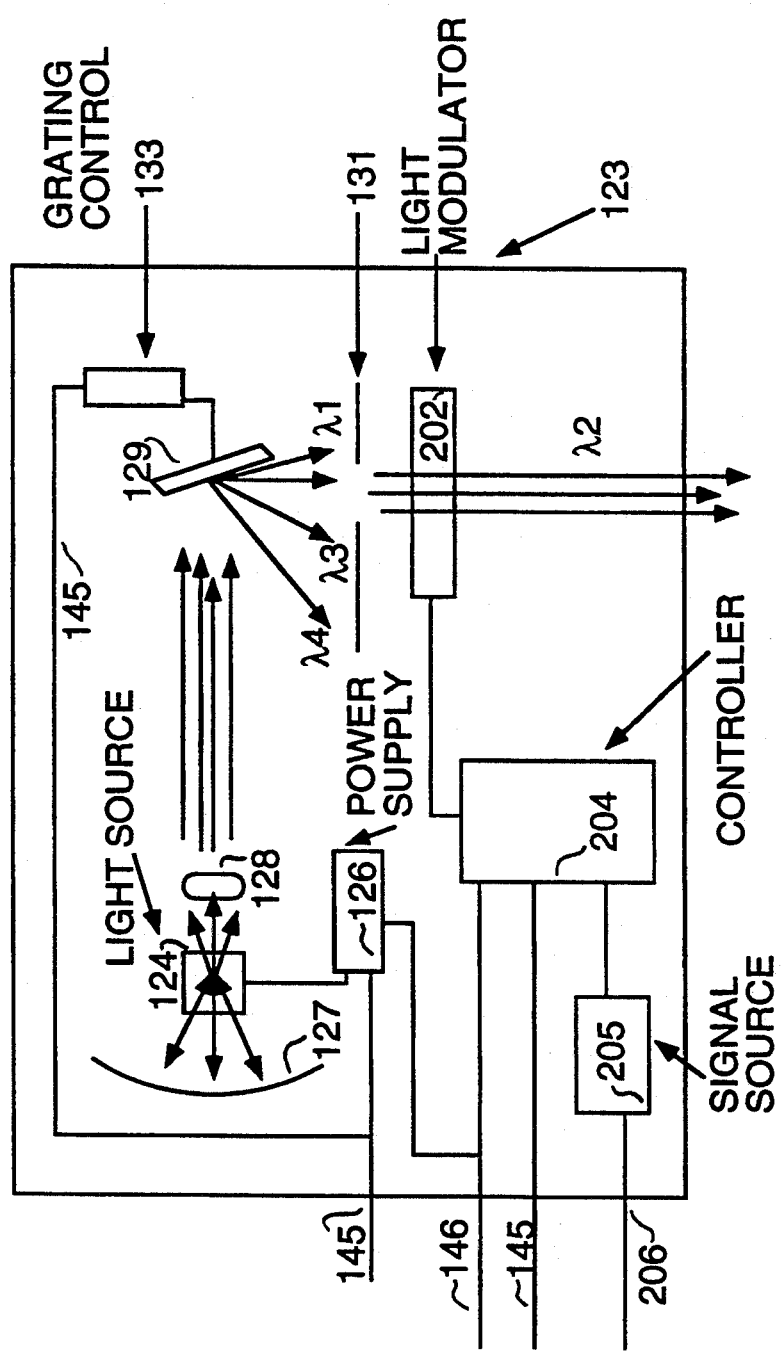
FIG. 8 is an illustration which shows a portion of the apparatus, particularly the light source assembly, associated with a second embodiment of the invention.

In a second embodiment of this invention, the light source assembly 123 of FIG. 2 is as shown in FIG. 8. In this embodiment source assembly 123 includes an intense light source 124 such as a xenon arc-lamp, for example Hamamatsu model L2274 or L2189 or a tungsten lamp, for example Hamamatsu model L2192. In this embodiment light source is effectively pulsed by means of a source power supply 126 to produce an optical pulse with a duration of approximately 10 ms ($10^{-2}$ seconds). In other embodiments this optical pulse duration may be shorter or longer and may even be continuous. The light source may consist of a pulsed lamp, or it may consist of a continuous light source followed in the optical system by a mechanical chopper wheel, shutter, or acousto-optic or electro-optic modulation device (not shown) for converting a continuous beam of light into a pulsed beam.

In this embodiment the light from the light source 124 is refocused by concave reflector 127 then collimated by a source lens 128. The geometry of the light source 124, concave reflector 127, and source lens 128, direct the radiation so that it is incident on a grating 129. Concave reflector 127 may have a spectrally selective reflective coating such that any undesirable spectral components, such as thermal infra-red spectral components, are not reflected into the source lens 128. Other spectral filters such as heat absorbing glass (not shown) may be similarly interposed in the optical system. Light which is incident on grating 129, is diffracted into a continuous spectra of component wavelengths. For example, $\lambda_1$, $\lambda_2$, $\lambda_3$, and $\lambda_4$, are four components of a beam containing a plurality of wavelength components which are differentially diffracted from a multi-spectral beam causing them to be spatially displaced from one another by the grating 129. Electromagnetic radiation (light in this case) of a specific wavelength is selected by aperture 131, which may have the form of a narrow slit, and then passes through modulator 202 before exiting assembly 123. Because the grating 129 spatially disperses the electromagnetic radiation, the grating control system 133 operates in conjunction with the aperture 131 so that the selected wavelength band passes through the aperture 131. This may be accomplished by mechanically translating the grating 129, by rotating the grating 129 through the appropriate angle, or by translating the aperture 131, modulator 202, lens 132, and optical fiber means 116 together so they intercept the desired portion of the dispersed electromagnetic beam. In other embodiments the grating may be replaced by a holographic grating, an acoustooptic tuneable filter, a set of filter wheels or prisms, or some other means of converting a broad band spectrum into tuneable narrow-band wavelength light. The grating is tuned by means of a grating control system 133. Both the grating control system 133 and the source power supply 126 are controlled by the computer 114.

There are several possible embodiments for the radiation source 124 of FIG. 8. These are essentially similar to those described for the first embodiment of this invention. Each of these alternative embodiments provides a source assembly 123 capable of providing light with a narrow band of wavelength in the range of 0.1–100 nm or less, which is tuneable on demand by the computer 114 over a broad frequency range.

In the embodiment illustrated in FIG. 8, having the xenon arc-lamp light source 124, the light is tuneable from about 500 nm to about 2500 nm, however, for other embodiments the light may be tuned over a narrower or wider range of wavelengths or over several discontinuous ranges. In this embodiment, the output of assembly 123 in FIG. 8 is therefore temporally modulated radiation having a controlled bandwidth and a controlled time varying center wavelength. The bandwidth should be chosen commensurate with the degree of precision needed in the measured absorption spectrum; narrow bandwidth radiation provides greater spectral resolution.

Figure 9:
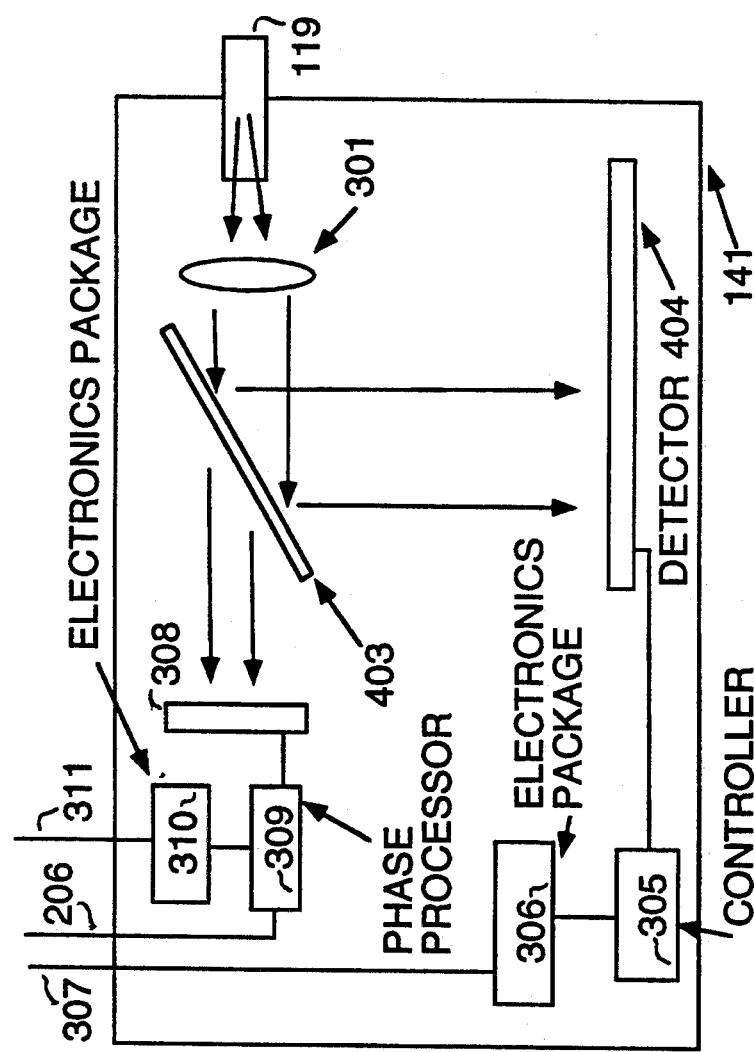
FIG. 9 is an illustration which shows a portion of the apparatus, particularly the detector assembly, associated with a second embodiment of the invention.

In this second embodiment, the detector assemblies 141 and 112 are again substantially equivalent to each other. The detector assembly 141 is illustrated in FIG. 9. The light entering the detector assembly 141 from fiber optic means 119 passes through a lens 301, from which it emerges as a collimated beam of light. This light is separated into two beams by a beamsplitter 403 in the form of a Fresnel reflector or other broadband partial reflector.

One of the two resultant beams is incident on a detector 404. In this embodiment: this detector is in the form of a silicon photodiode 404. This detector is typically a large area avalanche photodiode such as model TL15CA2 manufactured by Advanced Photonix, Inc. Alternatively, the detector may be a lead selenide or lead sulfide detector such as a model OTC 12S-8( )T or a model OTC-22S-8( )T detector manufactured by OptoElectronics Textron. These detectors may be thermoelectrically cooled, so as to reduce thermal noise and enhance sensitivity. In some embodiments these detectors might be replaced by photomultipliers for greater sensitivity. The choice of detector type is dependent on required wavelength sensitivity and available light intensities for a given application. In some embodiments where especially broad spectral coverage is required, multiple detectors of differing materials may be used, each sampling a portion of the wavelength dispersed beam.

The output from the detector 404 passes through the detector controller 305. The controller converts the detected light signals to electrical signals representing the light intensity incident on the detector as a function of wavelength emitted from assembly 123. These signals are processed in a conditioning electronics package 306 where they are processed and digitized prior to transmission to the computer 114 by means of cable 307.

The second beam transmitted through element 403 is incident on a detector 308 capable of generating time varying signals at the modulation frequency of the light. The detector 308 generates a time varying signal which is fed into an electronic processing unit 309, capable of measuring the phase delay between the detected optical signal and a reference signal derived from the light source assembly 123. After calibration of the system, the resultant output of this detection system is an array of values representing the average phase shift of detected light as a function of wavelength. These values are digitized and electronically processed in the electronics package 310 prior to transmission to the computer 114 by means of cable 311.

Detector assembly 112 is essentially identical to detector assembly 141. The light transmitted from clip assembly 101 by fiber optic means 108 is analyzed in detector assembly 112. The resultant output from assembly 112 is an array of measurements of intensity and phase delay as a function of wavelength.

The data collected by means of the second embodiment can be processed in essentially an identical manner to that collected by means of the first embodiment. The primary difference is that in the first embodiment data is collected simultaneously at all wavelengths, while in the second embodiment, wavelength data is collected sequentially as the light source output is scanned. The second embodiment thus requires longer to collect a given amount of data, but allows the use of single element detectors rather than arrays. This may be cheaper and allow increased detection sensitivity.

Figure 10:
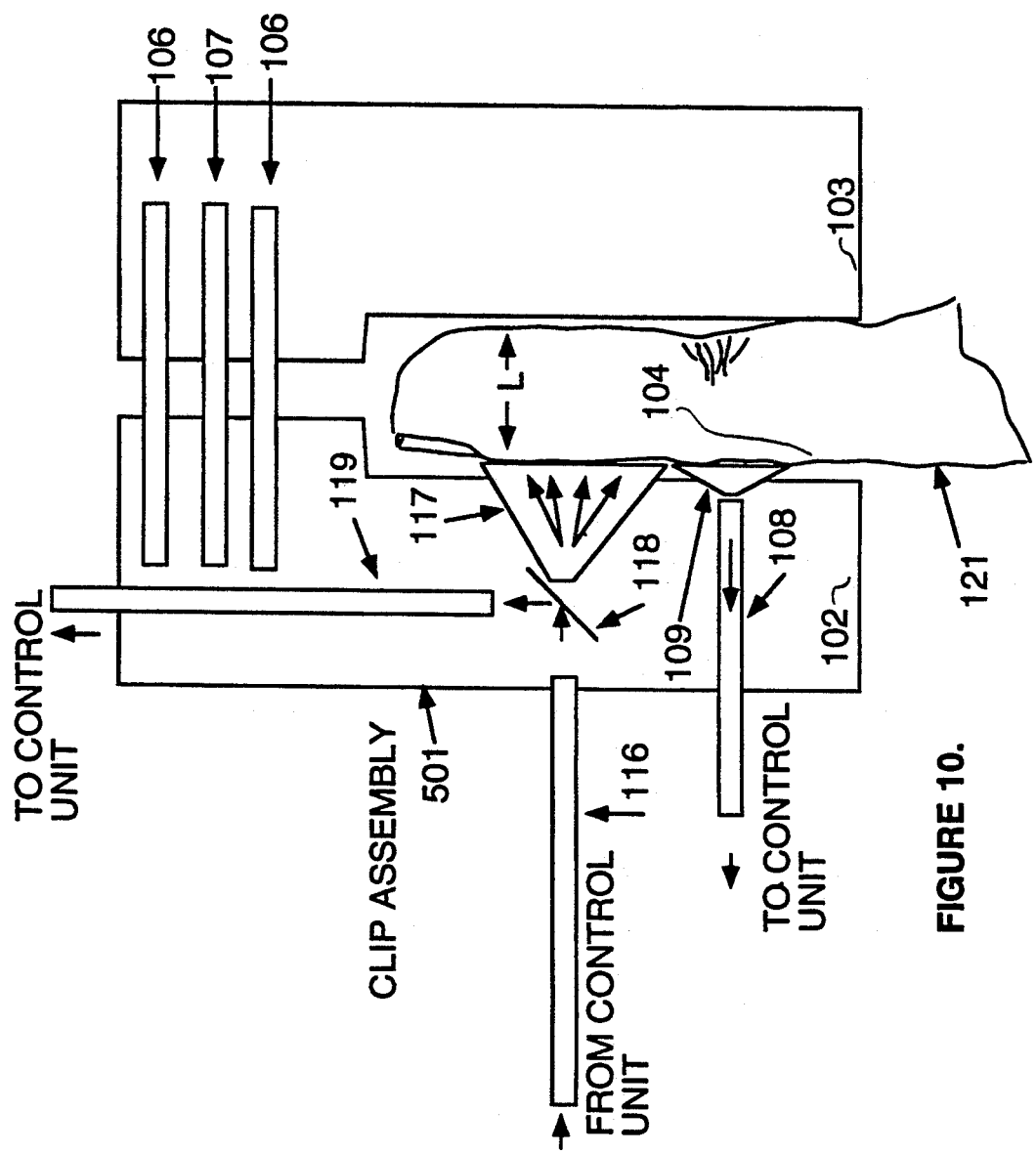
FIG. 10 is an illustration which shows a portion of the apparatus, particularly the clip assembly, associated with a third embodiment of the invention.

In a third embodiment of this invention clip assembly 101 of FIG. 1 is replaced by assembly 501 of FIG. 10. This assembly is similar to that of assembly 101, with elements performing the same function having the same identifying numbers. In contrast to assembly 101, the collection fiber optic means 108 is positioned on the same side of the tissue as illuminating fiber optic means 116. Light from means 116 enters the tissue, propagates a certain distance and is scattered one or several or many times. Eventually the light is re-emitted from the tissue sample 104, with a portion of it returning through the entry face 121 of the tissue. It is a portion of this emitted light which is collected by detection fiber optic means 108 and transmitted to control unit 111 in FIG. 2.

In a fourth embodiment of the invention, applicable to each of the first three embodiments described earlier, a signal is derived from the circulatory pulse of a patient undergoing analysis by means of this invention. Absorption data is collected so as to be synchronized with the circulatory pulse. By subtracting the background absorption at each wavelength from the absorption observed when the pulsatile blood flow causes maximum absorption, the measured absorption signal can be made to derive solely from arterial blood. This technique is well known in the field of pulse oximetry and can be extended to this invention to allow analysis of analytes in arterial blood alone even in the presence of multiple other absorbing species.

The process or method described may be practiced with a variety of apparatus and is not confined to the embodiments specifically enumerated and described.

What is claimed is:

1. The method of determining a measure of absorbance of electromagnetic energy per unit path length by chemical species within a medium that scatters and absorbs electromagnetic energy, comprising the steps of
   irradiating the medium with electromagnetic energy containing at least two components of different frequency, at least one of which is amplitude modulated;
   detecting electromagnetic energy emerging from said medium;
   measuring the intensity of the detected energy at each of said frequencies and comparing it to a measure of the irradiating intensity at each of said frequencies to provide a measure of absorbance of said energy at said different frequencies;
   determining from said at least one amplitude modulated component of the electromagnetic energy information relating to the path length travelled by said component; and
   deducing, from the measure of absorbance and the information relating to the path length travelled, a measure of absorbance per unit path length travelled by the radiation for each of said frequencies.

2. The method as in claim 1 including the step of converting said measure of absorbance of electromagnetic energy per unit path length travelled for each of said frequencies to a parameter related to the concentration of selected chemical species.

3. The method as in claim 2 including the step of correlating said parameter to a calibration model built by irradiating a medium having samples of varying composition including the chemical species, with electromagnetic energy at least two frequencies.

4. The method of claim 3 wherein said calibration model includes samples in which the concentration of each chemical species to be analyzed is independently varied and wherein said model includes samples representative of the extremes of anticipated concentrations of said chemicals as well as of samples that contain concentrations of said chemicals that covers the expected range of anticipated concentrations.

5. The methods of claims 3 or 4 in which sufficient independent frequencies of electromagnetic radiation are selected to separate changes in concentration of a chemical species to be analyzed from other interfering species present in the calibration sample set or expected to be present in the medium to be analyzed.

6. The method of claim 5 in which said quantitative measurement of at least one parameter related to the absolute or relative concentration of at least one chemical species consists of the absolute concentration of a chemical species or of the relative concentration of a chemical species expressed as a fraction of the concentration of a second chemical species or of a ratio of concentrations of two chemical species.

7. The method of claims 2, 3 or 4 in which said parameter is determined for a number of chemical species simultaneously.

8. The method of determining a parameter related to the absolute or relative concentration of a chemical species within a medium that scatters and absorbs electromagnetic radiation by a medium comprising the steps of
   generating electromagnetic radiation containing at least two components having differing frequencies;
   causing the temporal amplitude of at least one of said components to vary in a defined manner with time;
   introducing said electromagnetic radiation into said medium;
   detecting said electromagnetic radiation of said at least two components after it emerges from said medium;
   comparing the temporal amplitude variation of at least one of the detected components of said electromagnetic radiation with the temporal amplitude variation of at least one of the generated components of said electromagnetic radiation;
   determining from said comparison information relating to the path length travelled through the medium by at least one component of said radiation;
   measuring the intensity of at least two components of differing frequency of the detected electromagnetic radiation;
   comparing said measured intensities to the intensities of the introduced electromagnetic radiation to generate measures of the magnitudes of the absorbance of electromagnetic radiation by said medium at each of said at least two radiation frequencies; and
   deducing from said absorbance measures and said information relating to the path length travelled through the medium by said radiation measures of the absorbance of electromagnetic radiation by said medium per unit path length travelled by said radiation at each of said at least two radiation frequencies.

9. The method of claim 8 including the additional step of converting said measures of the absorbance of electromagnetic radiation by said medium per unit path length travelled by said radiation at each of said at least two radiation frequencies to provide quantitative measurement of at least one parameter related to the absolute or relative concentration of at least one chemical species the concentration of which can be correlated to the degree of scattering and absorption of said electromagnetic radiation by the medium.

10. The methods of claims 8 or 9 where said medium is a solid or a liquid or a gas or a mixture of one or more of said solid, liquid or gas.

11. The methods of claims 8 or 9 where said medium is a biological material.

12. The method of claim 11 where the chemical species to be analyzed in the medium is selected from the list of glucose, cholesterol, alcohol, bilirubin, ketones, fatty acids, lipoproteins, urea, albumin, creatinine, white blood cells, red blood cells, hemoglobin, blood oxygen, inorganic molecules, drugs and pharmaceutical compounds, water, oxygenated hemoglobin, cytochrome $(a,a_3)$, insulin, various proteins and chromophores, microcalcifications, and hormones.

13. The method of claim 12 wherein said medium is a portion of a mammal or contained within a portion of a mammal.

14. The method of claim 13 wherein said portion of a mammal is the head, finger, earlobe, tongue, or nasal septum.

15. The method of claim 13 wherein the resultant quantitative measurement of at least one parameter related to the absolute or relative concentration of at least one chemical species corresponds to the noninvasive measurement of that parameter.

16. The method of claims 8, 9, or 12 where the electromagnetic radiation is optical radiation.

17. The method of claims 8, 9, or 12 where the optical radiation consists of light with wavelengths between 200 nm and 20,000 nm.

18. The method of claims 8, 9, or 12 where the optical radiation consists of light with wavelengths between 400 nm and 3,000 nm.

19. The method of claims 8 or 9 wherein comparison of the temporal amplitude variation of at least one of the detected components of said electromagnetic radiation with the temporal amplitude variation of at least one of the generated components of said electromagnetic radiation consists of measurement of the phase shift or phase shifts between said at least one detected component of said electromagnetic radiation and said at least one generated component of said electromagnetic radiation.

20. The method of claim 8 where the amplitude of said at least one of said components of electromagnetic radiation is periodically amplitude modulated.

21. The method of claim 8 wherein the frequency of said periodic amplitude modulation is varied with time.

22. The method of claim 8 where the amplitude of said at least one of said components of electromagnetic radiation is essentially zero except for brief intervals of time with the result that said component of radiation is observed as a series of brief pulses of radiation.

23. The method of claim 22 wherein said pulses are repetitive with a fixed repetition frequency.

24. The method of claims 22 or 23 wherein comparison of the temporal amplitude variation of at least one of the detected components of said electromagnetic radiation with the temporal amplitude variation of at least one of the generated components of said electromagnetic radiation consists of measurement of the time delay between the introduction of said component of electromagnetic radiation into said medium and the detection of said component of electromagnetic radiation after it emerges from said medium.

25. The method of claims 22 or 23 wherein comparison of the temporal amplitude variation of at least one of the detected components of said electromagnetic radiation with the temporal amplitude variation of at least one of the generated components of said electromagnetic radiation consists of comparison of the temporal pulse shape of said detected components of said electromagnetic radiation with the temporal pulse shape of said generated components of said electromagnetic radiation.

26. The method of claims 8, 20, 21 or 22 wherein said temporal amplitude variation is rapid in comparison with the temporal separation between the introduction of said electromagnetic radiation into said medium and the detection of said electromagnetic radiation after it emerges from said medium.

27. The method of claims 8, 9, 20 or 21 wherein said component frequencies of electromagnetic radiation are selected to include multiple frequencies of electromagnetic radiation comprising a set of frequencies representative of the frequency range over which the interaction of the medium with electromagnetic radiation is to be examined.

28. An apparatus for determining a parameter related to the absolute or relative concentration of a chemical species within a medium that scatters and absorbs electromagnetic radiation comprising means for generating electromagnetic radiation containing at least two components of differing frequency;

means for causing the amplitude of at least one of said components to vary in a defined manner with time;

means for introducing said electromagnetic radiation into said medium;

means for detecting said electromagnetic radiation after it emerges from said medium;

means for comparing the temporal amplitude variation of at least one of the detected components of said electromagnetic radiation with the temporal amplitude variation of said at least one of the generated components of said electromagnetic radiation;

means for determining from said comparison information relating to the path length travelled through the medium by said at least one component of said radiation;

means for measuring the intensity of at least two components of differing frequency of the detected electromagnetic radiation;

means for comparing said measured intensities to the intensities of the introduced radiation to generate measures of the magnitudes of the absorbance of electromagnetic radiation by said medium at each of said at least two radiation frequencies; and means for deducing from said absorbance measures and said information relating to the path length travelled through the medium by said radiation measures of the absorbance of electromagnetic radiation by said medium per unit path length travelled by said radiation at each of said at least two radiation frequencies.

29. The apparatus of claim 28 including means for converting said measures of the absorbance of electromagnetic radiation by said medium per unit path length travelled by said radiation at each of at least two radiation frequencies to provide quantitative measurement of at least one parameter related to the absolute or relative concentration of at least one chemical species the concentration of which can be correlated to the degree of scattering and absorption of said electromagnetic radiation by the medium.

30. The apparatus of claim 28 where said means for causing the amplitude of at least one of said components of electromagnetic radiation to vary in a defined manner with time comprises means for periodic amplitude modulating said components.

31. The apparatus of claim 30 wherein said means for periodically modulating said components varies the frequency of said periodic amplitude modulation with time.

32. The apparatus of claim 31 wherein said means for comparing the temporal amplitude variation of at least one of the detected components of said electromagnetic radiation with the temporal amplitude variation of at least one of the generated components of said electromagnetic radiation comprises means for measuring the phase shift between said at least one detected component of said electromagnetic radiation and said generated component of said electromagnetic radiation.

33. The apparatus of claim 30 wherein said periodic amplitude modulation is at a rate which is high with respect to the temporal separation between the introduction of said electromagnetic radiation into said medium and the detection of said electromagnetic radiation after it emerges from said medium.

34. The apparatus of claim 28 wherein multiple frequencies of electromagnetic radiation are generated.

35. The apparatus of claim 34 where the electromagnetic radiation consists of light with wavelengths between 200 nm and 20,000 nm.

36. The apparatus of claim 34 where the electromagnetic radiation consists of light with wavelengths between 400 nm and 3,000 nm.

37. The apparatus of claim 35 where fiber optic means delivers the light to the medium.

38. The apparatus of claim 35 where fiber optic means collects the light entitled from the medium.

39. The method of determining a parameter related to the absolute or relative concentration of chemical species within a medium that scatters and absorbs electromagnetic energy, comprising the steps of irradiating the medium with elecromagnetic energy containing at least two components of different frequency, at least one of which is amplitude modulated;

detecting electromagnetic energy emerging from said medium;

measuring the intensity of the detected energy at each of said frequencies and comparing it to a measure of the irradiating intensity at each of said frequencies to provide a measure of absorbance of said energy at said different frequencies;

determining from said at least one amplitude modulated component of the electromagnetic energy information relating to the path length travelled by said component; and processing the measure of absorbance and the information relating to the path length travel led to obtain a parameter related to the absolute or relative concentration of a chemical species.

40. The method as in claim 39 including the step of correlating said parameter to a calibration model built by irradiating a medium having samples of varying composition including the chemical species, with electromagnetic energy at at least two frequencies.

41. The method of claim 40 wherein said calibration model includes samples in which the concentration of each chemical species to be analyzed is independently varied and wherein said model includes samples representative of the extremes of anticipated concentrations of said chemicals as well as of samples that contain concentrations of said chemicals that covers the expected range of anticipated concentrations.

42. The methods of claims 40 or 41 in which sufficient independent frequencies of electromagnetic radiation are selected to separate changes in concentration of a chemical species to be analyzed from other interfering species present in the calibration sample set or expected to be present in the medium to be analyzed.

43. The methods of claims 40 or 41 in which said quantitative measurement of at least one parameter related to the absolute or relative concentration of at least one chemical species consists of the absolute concentration of a chemical species or of the relative concentration of a chemical species expressed as a fraction of the concentration of a second chemical species or of a ratio of concentrations of two chemical species.

44. The method of claims 40 or 41 in which said parameter is determined for a number of chemical species simultaneously.

* * * * *